(12) United States Patent
Moore et al.

(10) Patent No.: US 12,111,298 B2
(45) Date of Patent: Oct. 8, 2024

(54) TRANSPORTABLE GAS DETECTOR UNIT HAVING MOUNTED GAS SOURCES FOR GAS SENSOR TESTING AND CALIBRATION

(71) Applicant: BLACKLINE SAFETY CORP., Alberta (CA)

(72) Inventors: Barry Moore, Alberta (CA); Phillip Benson, Alberta (CA); Cody Slater, Alberta (CA); Kirk Johnson, Alberta (CA); Allan Lester-Olivier, Alberta (CA)

(73) Assignee: BLACKLINE SAFETY CORP., Alberta (CA)

( * ) Notice: Subject to any disclaimer, the term of this patent is extended or adjusted under 35 U.S.C. 154(b) by 285 days.

(21) Appl. No.: 17/593,688

(22) PCT Filed: Mar. 16, 2020

(86) PCT No.: PCT/CA2020/050351
§ 371 (c)(1),
(2) Date: Sep. 22, 2021

(87) PCT Pub. No.: WO2020/191482
PCT Pub. Date: Oct. 1, 2020

(65) Prior Publication Data
US 2022/0163497 A1    May 26, 2022

Related U.S. Application Data

(60) Provisional application No. 62/822,623, filed on Mar. 22, 2019.

(51) Int. Cl.
*G01N 33/00* (2006.01)

(52) U.S. Cl.
CPC ..... *G01N 33/0016* (2013.01); *G01N 33/0006* (2013.01); *G01N 33/0032* (2013.01); *G01N 33/0062* (2013.01); *G01N 33/0068* (2024.05)

(58) Field of Classification Search
None
See application file for complete search history.

(56) References Cited

U.S. PATENT DOCUMENTS

| | | | |
|---|---|---|---|
| 5,239,492 A | 8/1993 | Hartwig et al. | |
| 6,428,684 B1 * | 8/2002 | Warburton | G01N 27/4163 204/406 |

(Continued)

FOREIGN PATENT DOCUMENTS

| | | |
|---|---|---|
| JP | 2017181173 A | 10/2017 |
| WO | 2016118355 A1 | 7/2016 |

(Continued)

OTHER PUBLICATIONS

ISA Canadian Intellectual Property Office, International Search Report Issued in Application No. PCT/CA2020/050351, Jun. 3, 2020, WIPO, 3 pages.

(Continued)

*Primary Examiner* — Brandi N Hopkins
*Assistant Examiner* — Nigel H Plumb
(74) *Attorney, Agent, or Firm* — McCoy Russell LLP

(57) ABSTRACT

The technology relates to a transportable gas detector unit configured to operate in a detection mode and a test mode for gas sensor testing and calibration. The transportable gas detector is configured with one or more gas sources mounted on the gas detector unit by mounting points to rigidly hold the gas sources in place when the gas detector unit is moved, enabling remote testing/calibration of gas sensors.

17 Claims, 3 Drawing Sheets

(56) References Cited

U.S. PATENT DOCUMENTS

| | | |
|---|---|---|
| 6,442,639 B1 | 8/2002 | McElhattan et al. |
| 6,997,347 B2 | 2/2006 | Peng et al. |
| 7,073,368 B2 | 7/2006 | Wood et al. |
| 7,530,255 B2 | 5/2009 | Frank et al. |
| 7,610,142 B1 | 10/2009 | Hoard et al. |
| 8,775,087 B1 | 7/2014 | Selman et al. |
| 9,019,117 B1 | 4/2015 | Crook |
| 9,245,436 B1 | 1/2016 | Crook |
| 9,488,627 B2 | 11/2016 | Skourlis |
| 9,508,243 B1 | 11/2016 | Crook |
| 9,784,755 B2 | 10/2017 | Scheffler et al. |
| 2005/0000981 A1 | 1/2005 | Peng et al. |
| 2005/0035869 A1 | 2/2005 | Crook |
| 2011/0197649 A1 | 8/2011 | Han et al. |
| 2014/0130569 A1 | 5/2014 | Doering |
| 2014/0284222 A1 | 9/2014 | Wanek, Jr. et al. |
| 2017/0003260 A1 | 1/2017 | Sloop et al. |
| 2017/0146501 A1 | 5/2017 | Martens et al. |
| 2017/0269044 A1* | 9/2017 | Diekmann ......... G01N 33/0011 |
| 2018/0017589 A1 | 1/2018 | Scheffler et al. |
| 2018/0202984 A1 | 7/2018 | Haase et al. |
| 2018/0267003 A1* | 9/2018 | Johnson ................. G08B 21/12 |
| 2018/0335410 A1 | 11/2018 | Martens et al. |
| 2019/0228631 A1* | 7/2019 | Stinson ................ G08B 25/005 |

FOREIGN PATENT DOCUMENTS

| | | | |
|---|---|---|---|
| WO | WO-2018068130 A1 * | 4/2018 | ............. G06Q 10/06 |
| WO | 2018192711 A1 | 10/2018 | |
| WO | 2019037748 A1 | 2/2019 | |

OTHER PUBLICATIONS

European Patent Office, Extended European Search Report Issued No. 20777517.2, Oct. 31, 2022, Germany, 11 pages.

ISA Canadian Intellectual Property Office, International Search Report Issued in Application No. PCT/CA2020/050351, Jun. 3, 2020, WIPO, 4 pages.

ISA Canadian Intellectual Property Office, Written Opinion of the International Searching Authority Issued in Application No. PCT/CA2020/050351, Jun. 3, 2020, WIPO, 7 pages.

* cited by examiner

TRANSPORTABLE GAS DETECTOR UNIT HAVING MOUNTED GAS SOURCES FOR GAS SENSOR TESTING AND CALIBRATION

CROSS REFERENCE TO RELATED APPLICATIONS

The present application is a U.S. National Phase of International Application No. PCT/CA2020/050351 entitled "GAS SENSOR TESTING APPARATUS AND METHODS," and filed on Mar. 16, 2020. International Application No. PCT/CA2020/050351 claims priority to U.S. Provisional Patent Application No. 62/822,623 filed on Mar. 22, 2019. The entire contents of each of the above-listed applications are hereby incorporated by reference for all purposes.

TECHNICAL FIELD

The disclosure relates to gas monitoring devices and associated methods and systems. The disclosure further relates to testing the status of the transportable gas detectors to help ensure that they are functioning properly.

BACKGROUND AND SUMMARY

Gas monitoring devices or gas detectors include devices which are configured to monitor a user or an environment in order to determine whether there is a danger.

In situations where there is a risk of hazardous gas, the area around the risk is monitored by gas measurement devices. In the industry, these devices are commonly referred to as "area monitors". These area monitors house gas sensors. The sensors detect the concentration levels of various gases. When the gas levels for a particular gas reach a predetermined threshold, the area monitor will signal with an alarm. The alarm typically consists of lights, sound and often remote transmission of the alert.

Generally, the sensors also require periodic calibration due to normal changes in sensitivity that sensors exhibit over their service life. A calibration is performed by exposing the monitor to a known concentration of gas for a defined length of time to adjust the sensor readings for accuracy.

U.S. Pat. No. 7,530,255 (Frank) discloses a testing module for use with a gas detector, includes a plurality of gas inlets and outlets, each outlet being in fluid connection with one of the inlets. Each of the outlets is adapted to mate with and form a fluid connection with one of the inlets of a second like testing module. Gases can then flow from the outlets of the testing module into the inlets of the second like testing module. A gas container module for use with a gas container, includes a plurality of gas inlets and outlets, each inlet being in fluid connection with one of the outlets. Each of the inlets is adapted to mate with and form a fluid connection with one of the outlets on a second like gas container module. Gases can then flow from the outlets of the second like gas container module into the inlets of the gas container module.

U.S. Pat. No. 8,775,087 (Selman) discloses a system which includes a gas processor with gas processor data storage and computer instructions to receive in various device protocols simultaneously information from rig-based sensors and gas analysis devices drilling data, calibrate the devices and graphically present the data using both time events and depth events.

U.S. Pat. No. 9,488,627 (Skourlis) discloses a stationary gas monitoring and testing system includes one or more gas monitoring stations, each of which includes at least one gas sensor. The system also includes a supply of testing span gas, a supply of testing zero gas, a gas distribution network connecting each gas sensor to the span gas supply and the zero-gas supply through substantially separate conduits, and a controller for enabling the delivery of gas from the supply into the network for delivery to the one or more sensors.

U.S. Pat. No. 9,784,755 (Scheffler) discloses a method of operating a sensor system including at least one sensor for detecting an analyte gas and a control system configured to electronically interrogate the sensor to determine the operational status and to initiate an automated calibration of the sensor with the analyte gas or a simulant gas.

In accordance with the present disclosure, there is provided a transportable gas detector comprising:
a controller;
one or more source inlets for connection to one or more gas sources;
a chamber comprising a gas-permeable section to allow gaseous communication with the outside environment and one or more source outlets configured to receive gas from the one or more source inlets;
a gas sensor in communication with the controller and positioned within the chamber;
a flow switch controlled by the controller, the flow switch configured to allow gas to be introduced directly into the chamber via the one or more source outlets;
a wireless transceiver configured to enable communication between the controller and a remote computer;
wherein the transportable gas detector is configured to:
in a detection mode, detect gases entering the chamber through the gas permeable portion from the outside environment; and
in a test mode, introduce gas via the one or more source outlets and test that the gas sensor is detecting the introduced gas.

It will be appreciated that the gas sources may be located outside the chamber. It will be appreciated that the gas sources may be located outside the gas detector. A said source inlet outside the chamber may be linked to a said source outlet inside the chamber by a gas conduit (e.g. a tube, channel or gas line) to allow the introduction of a gas into the chamber from an external gas source (e.g. outside the chamber).

The gas may be pumped through such a conduit with a pump. The pump may be inside or outside the chamber. Having gas inlets into the chamber mean that the test gas does not have to pass through the gas-permeable section which may reduce the risk of the test gas escaping. Because, the gas is introduced directly into the chamber, the gas-permeable section keeps the gas around the sensors which may reduce the amount of test gas required (e.g. without requiring extra mechanical parts to seal the chamber or gas-permeable section for testing). The pump may be configured to pump at a predetermined flow rate (e.g. regardless of the pressure differential between the source and the chamber). The pump may be configured to pump a predetermined quantity of gas into the chamber. This may allow the test to be more consistent. The conduit may comprise a fixed flow regulator.

The gas detector may comprise an environmental gas conduit with an environmental inlet which is open to the external environment, and an environmental outlet within the chamber. The environmental gas conduit may comprise a pump configured to pump environmental gas into the chamber in order to transition the gas detector from the test mode to the detection mode more quickly. The pump may pump the gas in the chamber out through the environmental gas conduit thereby sucking in gas through the gas permeable portion or to pump the gas in the chamber out through the gas permeable portion thereby sucking in gas through the environmental gas conduit. The pressure in the chamber may be monitored throughout this procedure to determine if the gas permeable portion is blocked.

Each gas conduit may comprise a flow switch for controlling whether gas can pass from the source inlet to the source outlet. A flow switch may comprise a solenoid switch.

The gas detector may comprise a pressure sensor within the chamber, wherein the gas detector is configured to measure the test-mode gas pressure within the chamber during test mode and transmit an alert in response to the test-mode gas pressure exceeding a predetermined threshold. In this case, once the gas is introduced, there will be a temporary increase in pressure before the excess pressure is dissipated by gas passing out through the gas-permeable section. The hole size and area of the gas-permeable section will dictate the shape and/or size of the pressure spike.

The gas detector may be configured to switch between the test mode and the detection mode in response to receiving a command remotely via the wireless transceiver.

The gas detector may be configured to switch autonomously and/or automatically between the test mode and the detection mode.

The chamber may have a volume of less than 100 $cm^3$. The chamber may have a volume of less than 50 $cm^3$. The gas permeable section may have an area of less than 50 $cm^2$. The gas permeable section may have an area of less than 20 $cm^2$. In the case of a mesh, the area of the gas permeable section is the overall area of mesh which is not blocked (e.g. it may correspond to the area of the hole to which the mesh is attached).

The effective depth of the chamber may be considered to be the volume of the chamber divided by the area of the gas permeable section. The effective depth of the chamber may provide an indication of how quickly the volume of gas within the chamber can be exchanged through the gas permeable section. The effective depth may be greater than 1 cm and/or less than 5 cm (e.g. 2.5 cm). How quickly gas may be exchanged may also be dependent on the nature of the permeable portion (e.g. the percentage open area of the mesh) and/or on the shape of the chamber.

The chamber be formed as an integral part of the gas detector housing. The gas-permeable portion may be exposed on the outside of the gas detector housing to allow gas from the environment to freely move into the chamber.

The gas permeable portion may comprise a mesh screen. The gas permeable portion may comprise a mesh screen with mesh openings of less than 150 microns. Mesh openings of less than 150 microns may provide improved wind protection. The mesh may have an open area of between 10-50%. The open area is expressed as a percent which indicates the portion of total screen area which is open space. It is dependent upon the mesh count and wire diameter.

It will be appreciated that chamber configuration including the optimum hole size may be a compromise between one or more of: reducing the effect of wind on the gas sensors; allowing free movement of gas from the environment into the chamber; restricting the flow of test gas out from the chamber; and allowing the pressure of the chamber to be measured.

The transportable gas detector may be configured to detect gases from a remote location by pumping gas from the remote location into the chamber via a gas line.

The transportable gas detector may be configured to:
preform a series of bump tests, each bump test comprising introducing a gas into the chamber and measuring the sensor response until a predetermined response threshold is reached;
measure trends in the measured sensor response for each bump test over time; and
determine when a calibration is due based on the determined trend.

The gas detector may be configured to:
preform a series of bump tests, each bump test comprising introducing a gas into the chamber and measuring the sensor response until a predetermined response threshold is reached;
measure trends in the measured sensor response for each bump test over time; and
determine when a sensor is nearing its end of life.

The end of a sensor's life may be when the sensitivity of the sensor to a particular gas drops below a predetermined threshold.

The gas detector may be configured to:
introduce a baseline gas into the chamber;
measure the response of a said sensor which is insensitive to the introduced baseline gas; and
determine the baseline for the said sensor based on the measured response to the introduced baseline gas.

The baseline may correspond to the response of the sensor in the absence of the gas to which the sensor is sensitive. The baseline may be subtracted from subsequent measurements to determine the level of to which the sensor is sensitive.

The gas detector may comprise a motion sensor.
The gas detector may comprise a wind sensor.
The gas detector may comprise a microphone.
The gas detector may comprise a microphone and a speaker configured to sound an audio alarm when activated by the controller, the microphone being configured to detect whether the audio alarm is sounding when activated.

The gas detector may comprise a pump configured to pump gases from one or more of the inlets into the chamber.

The gas detector may comprise a renewable energy generator (e.g. a solar panel, a wind energy converter).

The gas detector may comprise a plurality of gas sensors, each sensor being positioned within a separate chamber. This may allow the test gases to be selectively directed to the appropriate sensor. This may reduce the quantity of test gas required.

The gas detector may comprise a plurality of gas sensors, each sensor being positioned within a common chamber.

According to a further aspect, there is provided a gas detector comprising:
a controller;
one or more source inlets for connection to one or more gas sources;
a chamber comprising a gas-permeable section to allow gaseous communication with the outside environment and one or more source outlets configured to receive gas from the one or more source inlets;
a gas sensor in communication with the controller and positioned within the chamber;
a flow switch controlled by the controller, the flow switch configured to allow gas to be introduced directly into the chamber via the one or more source outlets;
wherein the gas detector is configured to:
in a detection mode, detect gases entering the chamber through the gas permeable portion from the outside environment; and in a test mode, enable gas to be introduced into the chamber from the one or more inlets and test that the gas sensor is detecting the introduced gas.

The gas permeable portion may comprise a mesh screen with mesh openings of less than 150 microns.

The gas detector may comprise a pressure sensor within the chamber, wherein the gas detector is configured to measure the test-mode gas pressure within the chamber during test mode and transmit an alert in response to the test-mode gas pressure exceeding a predetermined threshold. The threshold may correspond to the gas-permeable section becoming blocked (e.g. by being covered by between 50-100%). It will be appreciated that there are a variety of ways of configuring the pressure sensor to measure a pressure corresponding to the chamber pressure. For example, the pressure sensor may be configured to be in the chamber, to be in fluid connection with the chamber, and/or to be in a region with a pressure which is equalized to the chamber pressure.

The chamber may comprise impermeable walls in addition to a gas-permeable section. In a detection mode, the chamber may be configured to be impermeable to gas except for the gas-permeable section. All the chamber walls may be gas-permeable.

According to a further aspect, there is provided a transportable gas detector comprising:

a controller;

a gas sensor in communication with the controller;

a wireless transceiver configured to enable communication between the controller and a remote computer;

a location detector configured to determine the location of the gas monitor; and a handle for lifting the gas detector, the handle having a handle switch which is activated when the gas detector is lifted, wherein the transportable gas detector is configured to transmit location information to the remote computer in response to the handle being released.

A transportable gas detector is generally not designed to be worn on the users clothing. A transportable gas detector may be designed to be moved from one location to another then remain stationary while in use. A transportable gas detector may be greater than 1 kg. A transportable gas detector may have a battery life greater than 24 hours. A transportable gas detector may be connected to other fixed or temporary power sources. A transportable gas detector may control other fixed or temporary electronic devices.

The gas monitor may comprise a location detector configured to determine the location of the gas monitor. The gas monitor may be configured to transmit the determined location of the gas detector to the remote computer in response to the measured environmental or user parameters going beyond a predetermined range.

A transportable gas detector may comprise a handle for lifting the gas detector, the handle having a handle switch which is activated when the gas detector is lifted; and wherein the transportable gas detector may be configured to transmit location information to the remote computer in response to the handle being released. For example, when the weight of the transportable gas detector is carried by the handle, the weight may activate the handle switch. The handle switch may be a push switch (e.g. located on the underside of the handle or the side on which the weight is applied when the detector is carried). This may allow the location of the detector to be more easily monitored each time it is moved by a user (e.g. whether the move is authorised or not). The transportable gas detector may be configured to transmit location information to the remote computer in response to the handle being released for a predetermined period of time (e.g. between 1 and 20 minutes). This may prevent location information being transmitted multiple times as the user is positioning the transportable gas detector in the desired position (e.g. when readjusting the position using the handles).

Because transportable gas detectors are configured to be moveable but also to be left in one location for a prolonged period of time, there is a risk that the location is not recorded (e.g. if employees move the transportable monitor out of there way to do other work). The gas monitor may be configured to transmit the determined location of the gas detector. The gas monitor may be configured to transmit the determined location of the gas detector periodically (e.g. once per hour or once per day). The gas monitor may be configured to transmit the determined location of the gas detector to the remote computer in response to one of the sensors failing a test carried out in the test mode and/or if the alarm is activated and/or an unsafe level of gas is detected in the detection mode. This may allow the gas monitor to be more easily located by service staff or rescue personnel e.g. when checking on the gas monitor. Also, receiving the location of the gas monitor may allow a remote computer or a user of the remote computer to know if the monitor is moved because, for example, if the gas monitors were placed in a particular location for a reason (e.g. near a gas line or potential leak), the location can be dangerous if unmonitored.

The gas detector may be configured to send an alarm-mode signal to the remote computer to notify the remote computer that the alarm of the gas detector has been activated.

The gas detector may comprise a speaker (e.g. for sounding an audio alarm and/or for communications). The gas detector may comprise a light (e.g. for providing a visual alarm).

The gas detector may be configured to enable (e.g. initiate) two-way communication with the remote computer in response to a user interaction or an alarm being activated.

The gas detector may comprise mounting points for the one or more gas sources, the mounting points being configured to rigidly hold the gas sources (e.g. gas cylinders) in place. Therefore, if the transportable gas detector is moved, the gas sources can be more easily moved with the gas detector.

A gas source may be considered to be a container for gases. A gas source may be a gas cylinder or tank. A gas source may be a pressure vessel for storage and containment of gases at above atmospheric pressure. High-pressure gas cylinders are also called bottles. Inside a gas source the stored contents may be in a state of compressed gas, vapor over liquid, supercritical fluid, or dissolved in a substrate material. A typical gas cylinder design is elongated, standing upright on a flattened bottom end, with the valve and fitting at the top for connecting to the gas inlet.

The transceiver may be configured to use wired or wireless communication. The transceiver may be configured to use one or more of: cellular radio Satellite communication, wide-area network (WAN), infrared, BlueTooth™ and Wi-Fi.

The gas monitor may be configured to communicate with a remote computer. The remote computer may be a remote server. The server may be monitored by a plurality of computing devices connectable to the remote server. This allows one alert on the server to be seen by multiple potential helpers via the computing devices. The remote server may be configured to store data received from the gas monitor in alert mode (e.g. including the two-way (e.g. voice or text) communication, threat data, location of user and/or time of threat being detected).

The gas monitor may be configured to enable multiple modes of voice communication.

The gas monitor may be configured to transmit information to the remote computer in response to the battery level going below a predetermined threshold (e.g. when the battery is about to run out) and/or in response to the amount of gas in the gas sources going below a predetermined threshold (e.g. when there is insufficient gas in a source to perform a test). The gas monitor may be configured to transmit battery and/or gas source information to the remote computer (e.g. periodically or upon request). The gas monitor may be configured to display battery and/or gas source information.

The remote computer may be a central server, cloud or other device. The remote computer (e.g. cloud) may make the information available at a variety of terminals (e.g. smartphone or computer via a log-in) via the internet.

The gas monitor may comprise a location detector. The location detector may comprise: a GPS module. The location detector may be configured to use local fixed-point anchor-node signaling to determine location (e.g. fixed Wi-Fi points). The location detector may use cellular networks to determine location. The location detector may comprise an indoor positioning system (IPS).

The one or more threat sensor may be configured to sense one or more of the following environmental parameters: concentration of a particular gas; airflow; temperature of the environment; humidity; radiant heat; sound intensity and light intensity.

A monitoring gas monitor may include one or more of: a gas sensor, processing circuitry, one or more motion or accelerometer sensors, one or more gyroscope or shock sensors, one or more two-way communication modules, one or more physiological sensors, one or more mode sensors, transmitter circuitry and receiver circuitry.

The gas monitor or system may comprise processing circuitry to calculate, assess and/or determine the conditions on sensor data. The processing circuitry may include memory (for example, Flash memory, DRAM and/or SRAM) to store, and transmitter circuitry to send and receive information over the cellular, satellite or other such communication network, said sensor data and information which is representative of environmental conditions (for example, atmospheric carbon dioxide). The gas monitor, machine(s), processor(s) (suitably programmed) and/or field programmable gateways (or combinations of the aforementioned)) may be employed to calculate, determine, assess and/or determine the environmental risks for the user based on sensor data.

Sensors and networking circuits may include, for example, one or more accelerometers, gyroscopes, compasses, global positioning system receiver, short range wireless circuits which may include ANT or Bluetooth™ or other short-range protocols, multicast wireless sensor, to calculate and/or detect the location of the user and transmit sensor data. Some gas monitors are configured to use, for example, 3G and satellite wireless connections. This mitigates the need for Wi-Fi networks, infrastructure and/or Bluetooth™ connections.

The gas detector may be configured to enable the processes of generating alerts based on pre-determined levels or sensor thresholds.

The gas detector may be configured to enable the processes of two-way communication based on transmission or triggering of pre-determined levels or sensor thresholds.

The gas detector may be configured to use interchangeable sensors. The gas monitor or system may be configured to use integrated sensors.

The gas detector may comprise a user interface. The user interface may include one or more output mechanisms (for example, a display and/or speaker) and/or one or more input mechanisms (for example, a microphone, and sensor and tactile gesture recognition sensor(s)); notably, any manner of and/or mechanism for outputting and/or inputting of data and/or commands (for example, responses to, for example, queries) are intended to fall within the scope of the present disclosure.

The gas detector may comprise a single unit. The gas monitor may comprise multiple units in communication with each other. For example, the gas monitor system may comprise a gas detector unit in communication (e.g. wireless communication such as Bluetooth™) with a portable electronic device with a controller and a transmitter (e.g. a mobile phone or laptop).

A gas detector may comprise a controller comprising a processor and a memory having computer program code. A remote computer may comprise a controller comprising a processor and a memory having computer program code.

Also encompassed within the present disclosure are corresponding methods for using the gas detectors and systems described above.

Also encompassed within the present disclosure are computer programs for configuring the gas detectors and systems described above to perform their functions. Such computer programs may be stored on non-transitory media such as CDs.

In some cases, it will be appreciated that this technology may be applied to portable gas detectors and portable personal gas detectors in addition to transportable gas detectors.

BRIEF DESCRIPTION OF THE FIGURES

Various objects and features of the disclosure will be apparent from the following description of certain embodiments of the disclosure, as illustrated in the accompanying drawings. The drawings are not necessarily to scale, emphasis instead being placed upon illustrating the principles of various embodiments of the disclosure. Similar reference numerals indicate similar components.

FIG. 1b is a schematic view of the Internal components of the area monitor of FIG. 1a.

DETAILED DESCRIPTION

Introduction

Figure 1A:
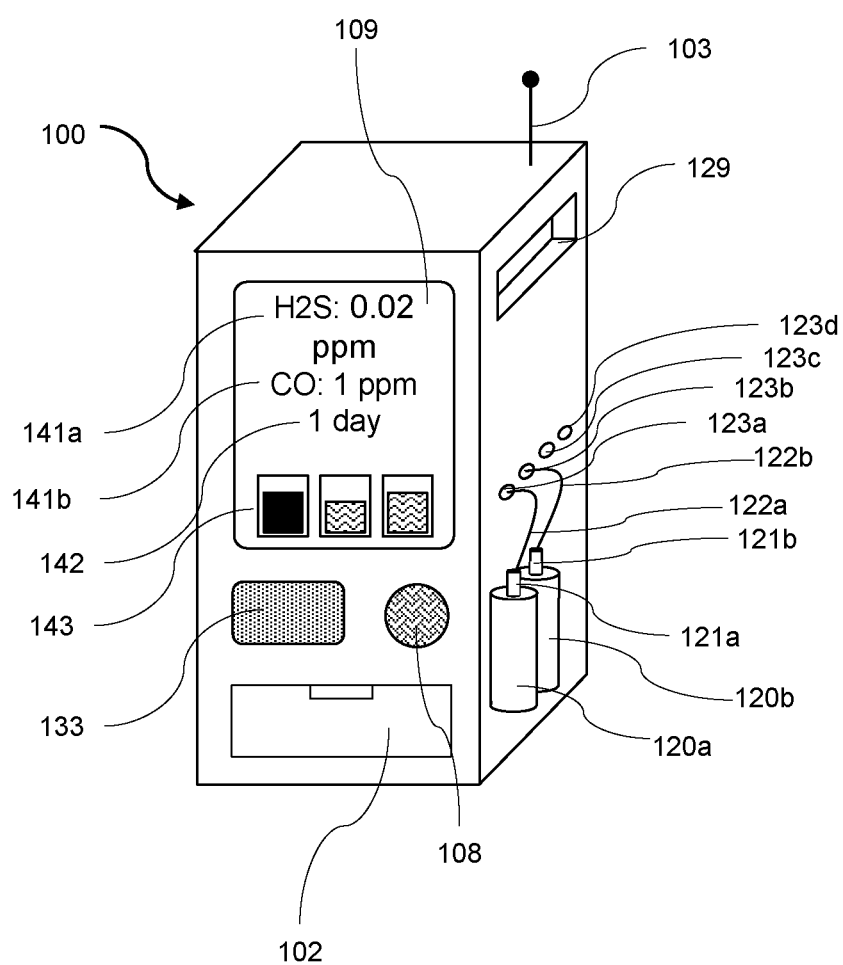
FIG. 1a is a schematic view showing the external arrangement of area monitor with bump and calibration equipment according to one embodiment.

Various aspects of the disclosure will now be described with reference to the figures. For the purposes of illustration, components depicted in the figures are not necessarily drawn to scale. Instead, emphasis is placed on highlighting the various contributions of the components to the functionality of various aspects of the disclosure. A number of possible alternative features are introduced during the course of this description. It is to be understood that, according to the knowledge and judgment of persons skilled in the art, such alternative features may be substituted in various combinations to arrive at different embodiments of the present disclosure.

Industrial chemicals leaked, spilled, or mishandled are common risks within environments such as manufacturing facilities. These facilities may have incorporated real-time gas detection monitors with man-down alarms. Such an industrial facility may provide monitoring capability of remote situations, in multiple locations, and across multiple platforms or geographies.

There are three categories of gas detection:
1. Portable: designed to carried by the user
2. Transportable, moveable but designed to be set in place for an extended period of time (days to months); and
3. Fixed: designed to be permanently in place.

The present technology relates primarily to transportable gas detectors (although aspects may also be applicable to fixed and portable gas detectors). It is important to ensure that transportable gas detectors are regularly calibrated and tested because, unlike portable detectors, they are not regularly returned to a home base which may have dedicated testing equipment and, unlike fixed detectors, they are not incorporated into a network (e.g. comprising gas, power and/or wired communication connections) which provides a consistent environment and the possibility of regular testing via the network.

All gas detectors should generally be regularly tested for functional capability to determine if they respond to targeted gases, called a bump test. A bump test is a brief exposure of the monitor to gas in order to verify that the sensors respond and that the instrument alarms function accordingly. The sensors also require periodic calibration due to normal changes in sensitivity that sensors exhibit over their service life. A calibration is generally performed by exposing the monitor to a known concentration of gas for a defined length of time to adjust the sensor readings for accuracy.

Bump testing is typically performed on the sensors once a day. Calibration is generally done once every 30 to 180 days depending on the system.

The technology described herein provides a method and apparatus for a gas monitor that can initiate and perform its own baseline (zeroing), bump test and/or calibration. This technology reduces or eliminates the need for manually initiated bump tests or calibrations as well as reducing or eliminating the need for interfacing with a docking station. This will allow the gas monitor to be remotely tested and maintained in the field for extended lengths of time without human intervention.

The technology does this by incorporating containers for gas (e.g. $CO_2$, $NH_4$) into the transportable gas detector. Gas from these containers can be introduced into a chamber containing the sensor to test whether the sensor is still working. When not being tested, the gas detector is configured to monitor gas from the environment which enters the chamber through a gas-permeable section (e.g. a mesh portion).

The inventors have recognized a need for improved monitoring systems to improve the detection of threats and to improve the ability for users and others to respond when a threat is detected. In the course of the detailed description to follow, reference will be made to the attached drawings. These drawings show different aspects of the monitoring systems and, where appropriate, reference numerals illustrating like structures, components, materials and/or elements in different figures are labeled similarly. It is understood that various combinations of the structures, components, and/or elements, other than those specifically shown, are contemplated and are within the scope of the present disclosure.

Such a gas monitor may be useful for plant turnarounds. The term "plant turnaround" is used when large parts of an industrial plant (refinery, petrochemical plant, power plant, pulp and paper mill, etc.) shuts down operations an extended period to fix, upgrade or retrofit large industrial equipment.

Due to the risk of hazardous gas exposure during a plant turnaround, forty or more transportable gas detectors (also known as area monitoring devices) may typically be deployed. Generally, each day an employee is required to bump test or calibrate these gas detectors. They will need to travel though the entire turnaround area with a cylinder of gas and a fixed flow regulator to manually apply gas to each of the area monitors.

If the area monitor was able to perform bump tests and calibrations for itself, the operator would not be required to travel though potentially dangerous areas of the facility. That is, automatic testing may reduce the risk for employees.

In addition, area monitors are sometimes deployed around remote industrial infrastructure. For example, a gas well head, pipeline, or compressor station. These setups are often in remote locations, sometimes many kilometers from employees.

These remote deployments still require the area monitors to be bump tested and calibrated on a regular basis. To do this, employees need to travel to report locations, often alone to apply gas to the area monitors.

If the area monitor was able to perform bump tests and calibrations for itself, the operator would not be required to travel long distances in potentially poor driving conditions at regular intervals.

Moreover, there are many aspects and embodiments of the technology described and illustrated herein. The present disclosure is neither limited to any single aspect nor embodiment thereof, nor to any combinations and/or permutations of such aspects and/or embodiments. Moreover, each of the aspects of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein.

Area Monitor

Area monitoring devices of transportable gas detectors are often placed out in a working environment for extended periods of time. Area monitors can generally last a number of days on their internal battery, or if equipped with an electrical supply such as a solar panel (or other renewable source) they can be left indefinitely to detect gas in the area.

Once connected to a power supply, one factor potentially limiting the amount of time the area monitor can be left unattended is the bump test and calibration schedule. Since the gas sensors require periodic gas application, a human operator must generally visit each area monitor to manually perform these tests.

A transportable gas detector which is able to perform its own bump test and calibrate itself may mitigate the need for human operators to visit the transportable gas detector.

Figure 1B:
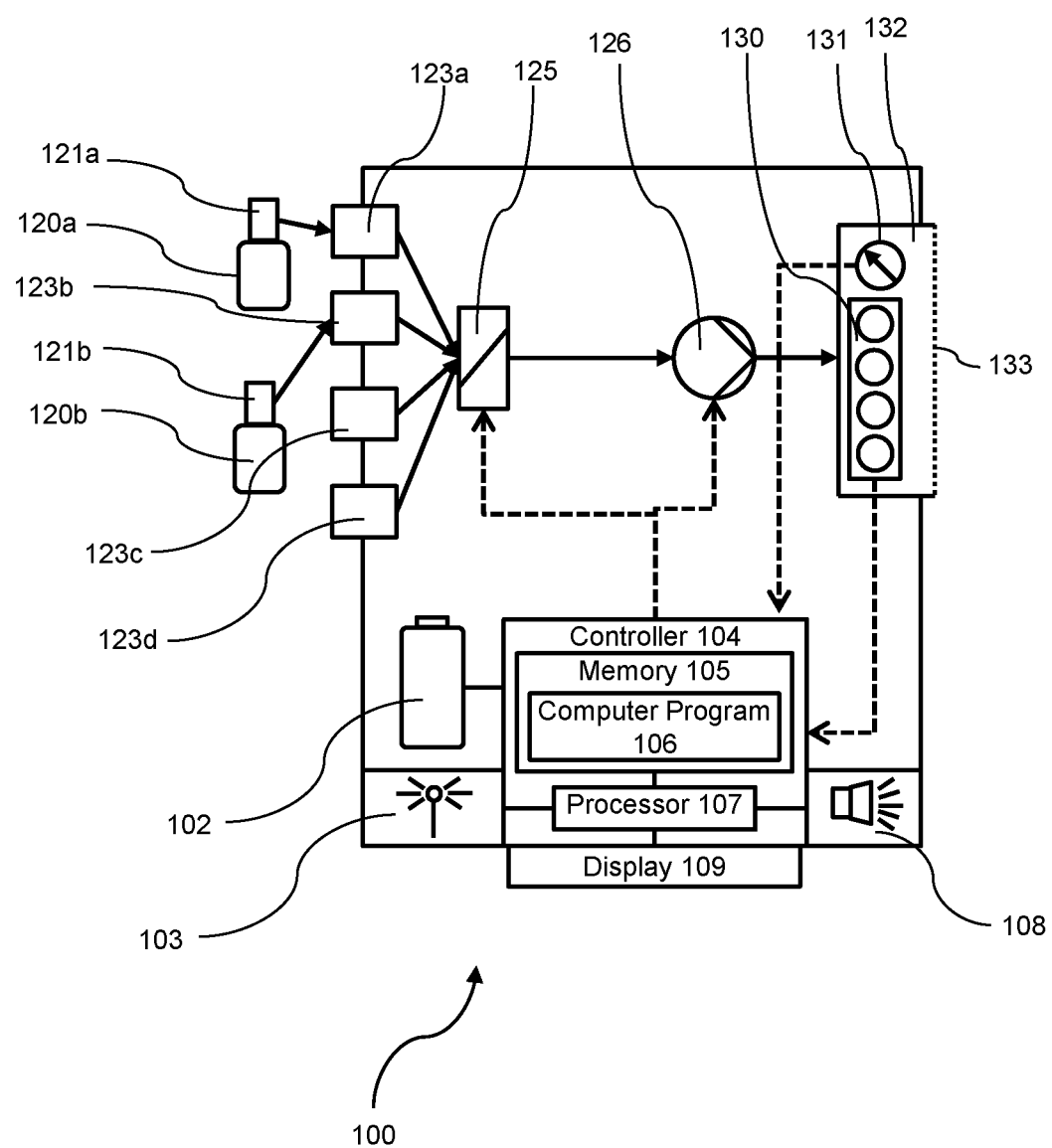

FIGS. 1a and 1b show a transportable gas detector 100 comprising:
a controller 104;
an integrated gas sensor 130 in communication with the controller and positioned within a chamber 132, the chamber comprising a gas-permeable section 133 to allow gaseous communication with the outside environment;

one or more inlets 123a-d for connection to one or more gas sources 120a-b;

a pump 126 controlled by the controller 104, the pump configured to pump gas from the one or more inlets into the chamber;

a wireless transceiver 103 configured to enable communication with the controller 104;

wherein the transportable gas detector is configured to:

in a detection mode, detect gases entering the chamber through the gas permeable portion from the outside environment without use of the pump; and in a test mode, pump gas into the chamber from the one or more inlets and test that the gas sensor is detecting the pumped gas.

In this case, the transportable gas detector is powered by an internal battery 102. The controller 104 in this case comprises a processor 107 and memory 105 storing computer program code 106. The computer program code is used to control operation of the transportable gas detector.

In the detection mode gas is not introduced into the chamber from the gas sources 120a-b (e.g. by blocking the gas conduits from the gas sources). Instead, the gas monitor is configured to detect gas passing through the gas-permeable section 133 and into the chamber 132. It will be appreciated that the gas-permeable section 133 may be a passive component which allows gas to move from the environment into the chamber without, for example, pumping.

The gas permeable section in this case has an area of 16 cm$^2$. In this case, when in a detection mode, if the level of a particular gas meets a predetermined criterion (e.g. if the level of $H_2S$ is too high or the $O_2$ level is too low), the controller is configured to activate a local alarm (e.g. an audio-visual alarm via display 109 and speaker 108). The gas monitor is also configured to transmit the alarm information via wireless transceiver 103. The alarm information may include location information. This allows a remote computer or remote device to monitor the gas monitor and react accordingly. For example, the remote computer may be configured to alert users nearby and/or send a rescue team.

In the situation in FIG. 1a, the gas monitor is in a detection mode. In this case, the gas monitor is configured to detect the levels of CO and the levels of $H_2S$. These detected gas levels 141a-b are shown on display 109. In this case, the gas monitor is also configured to display how long it has been 142 since the last test (e.g. bump test or calibration), and the level of remaining battery and gas level 143 in the two reservoirs 120a-b.

In this case, the gas monitor comprises four inlets 123a-d and four gas detectors mounted on a gas sensor array 130. In the situation shown in FIGS. 1a and 1b, gas cylinders 120a-b are attached to two of the inlets by gas lines 122a-b. Each gas cylinder 120a-b is fitted with a demand flow regulator 121a, 121b. In other embodiments, the gas monitor may be configured to detect one or more of: hydrogen sulphide, carbon monoxide, oxygen, ammonia, sulphur dioxide, chlorine, chlorine dioxide, carbon dioxide and volatile organic compounds. Other embodiments may be able to detect combustible material, Lower Explosive Limit (LEL) and radiation.

To bump test the gas sensor, the controller is configured to control a flow switch 125 (in this case a solenoid switch) for controlling which gas is introduced into the chamber. For example, if the carbon monoxide sensor was to be tested, the flow switch would be activated to allow pump 126 to pump carbon monoxide gas from the carbon monoxide reservoir 120a. Then, when hydrogen sulfide is to be tested, the flow switch would be switched so that the pump 126 would pump hydrogen sulfide gas from the hydrogen sulfide reservoir 120b. The chamber in this case has a volume of 40 cm$^3$.

In this case, the chamber 132 comprises a source outlet for introducing the test gas directly into the chamber which houses the sensor array 130. That is, in this case, the test gas does not have to pass through the permeable portion in order to enter chamber 132. The chamber serves to constrain the test gases for a time close to the sensors and limit the dispersion of the test gases (e.g. such as in windy conditions), which could lead to the gas monitor falsely reporting that the sensor was no longer sensitive to the test gas. Over a longer period of time, the test gases will disperse through the gas-permeable section 133 of the chamber to allow the gas monitor to return to a detection mode.

To help ensure reproducibility of the results, some embodiments may be configured to purge the chamber 132 with environmental gas. This may be achieved by using the pump to pump gas away from the chamber thereby sucking air through the gas-permeable section or by pumping gas through an inlet which is not connected to a gas reservoir. Other embodiments may be configured to purge the chamber 132 with a standard non-test gas prior to introducing a test gas into the chamber.

The gas permeable portion comprises a mesh screen with mesh openings of less than 150 microns (e.g. 100 microns or less). Having a mesh size of less than 150 microns may help shelter the gas sensors from the effects of wind. In this case, the mesh used is Sefar America Inc, 07-44/25: Polyester Mesh Filtering Screen 44 microns with an Open Area of 25%. As the open area is 25% and the area of the gas permeable section is 16 cm$^2$, the open area of the gas permeable section in this case is 4 cm$^2$.

In some embodiments, the gas monitor may not comprise a pump and instead rely on pressure from the test-gas reservoir to impel the test gas into the chamber.

In some embodiments, the gas monitor may comprise an individual pump, each pump being configured to introduce a separate gas.

In this case, the transportable gas detector comprises a pressure sensor 131 within the chamber, wherein the gas detector is configured to measure the test-mode gas pressure within the chamber during test mode and transmit an alert in response to the test-mode gas pressure meeting a predetermined criterion. By measuring the pressure when a test gas is being introduced into the chamber, the permeability of the gas-permeable section 133 can be determined. For example, if the gas-permeable section has become blocked (e.g. with dust or snow or by being positioned close to another object), then the gas detector may not be detecting the gases present in the environment, but instead be repeatedly detecting gases trapped in the chamber.

In some embodiments, the predetermined criterion could be the pressure exerted by the introduced gas being too high (e.g. exceeding a predetermined threshold) and/or the pressure decaying at too slow a rate after gas introduction has ceased. It will be appreciated that some embodiments may be configured to measure the pressure inside the chamber when gas is not being introduced in order to take a baseline pressure measurement. In such embodiments, the predetermined criterion for test-mode gas pressure may be based on the difference between the test-mode gas pressure and the baseline gas pressure.

In this case, the transportable gas detector is configured to switch between the test mode and the detection mode in response to receiving a command remotely via the wireless transceiver. This allows the transportable gas detector to be tested according to an arbitrary schedule without a site visit. This may also this allow the testing schedule to be adjusted without a site visit.

Other embodiments may be configured to switch autonomously between the test mode and the detection mode. For example, the transportable gas detector may be configured to test the gas sensors according to a predetermined schedule and/or based on previous test results (e.g. if the sensor is becoming less sensitive to the test gas, the detector may be configured to increase the testing frequency).

In this case, the gas detector comprises a handle 129 for lifting the gas detector, the handle having a handle switch which is activated when the gas detector is lifted. The transportable gas detector is configured to transmit location information to the remote computer in response to the handle being released. For example, when the weight of the transportable gas detector is carried by the handle, the weight may activate the handle switch.

Testing Mode

In the testing mode, in this case, the gas monitor is configured to deactivate the alarm to prevent the alarm being activated when test gas is introduced into the chamber. Other embodiments may be configured to activate the alarm during test mode to confirm to those in the vicinity that the gas monitor is working.

Other embodiments may comprise a microphone configured to determine whether the audio alarm is sounding when activated by the controller. For example, when the alarm is activated by the controller, the controller may be configured to determine whether a sound corresponding to the alarm (e.g. having the correct volume and frequency) is detected by the microphone. If the audio alarm is not detected by the microphone, the controller may alert the remote computer via the transceiver.

In this embodiment, the testing mode is initiated by introducing a test gas into the chamber. This may be physically detected by a pressure increase detected by the pressure sensor 131. If a pressure increase is not detected, the gas monitor may be configured to determine that the test has not been successful (e.g. due to gas not entering the chamber or exiting the chamber too quickly). This may be reported to a remote computer via the transceiver 103.

Figure 2:
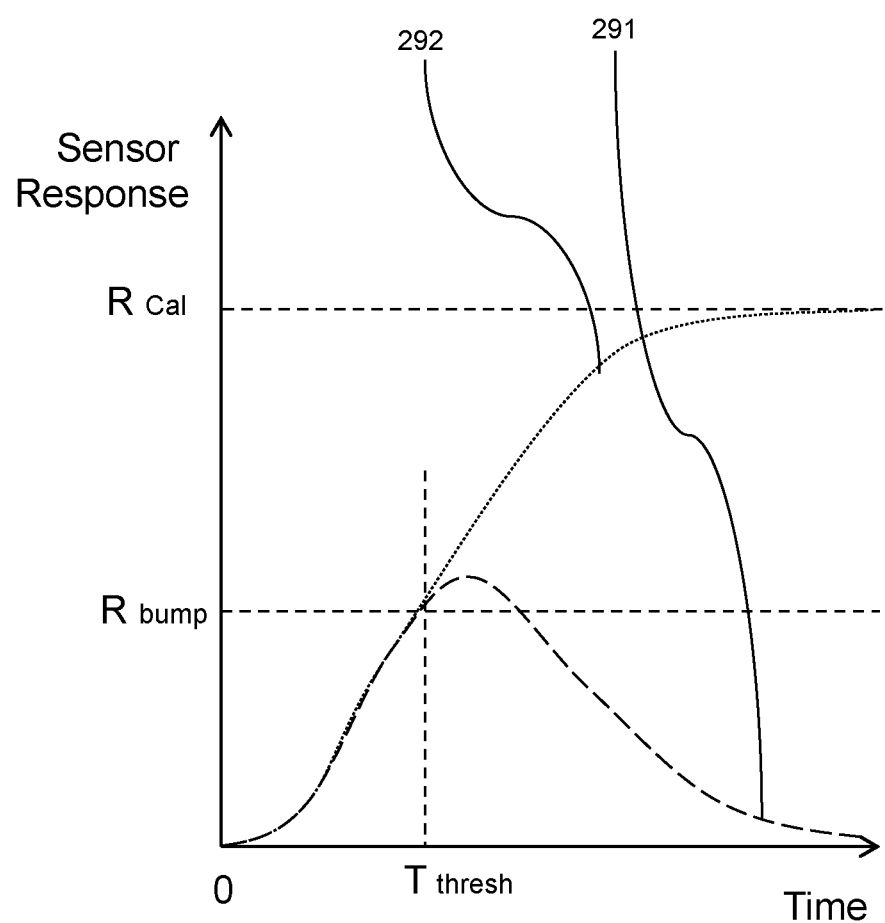
FIG. 2 is a graph showing the response of a sensor of the embodiment of FIG. 1a to the introduction of a test gas during a bump test and during a calibration test.

For a bump test, the gas monitor is configured to monitor the response of the corresponding gas sensor (e.g. the CO sensor when CO is introduced into the chamber). The bump test curve 291 is shown in FIG. 2. In this case, the gas monitor is configured to determine whether the response of the gas sensor is greater than a predetermined bump threshold. Once the gas sensor meets the predetermined threshold, the gas monitor is configured to stop introducing gas and report that the gas sensor is still sufficiently sensitive. This is shown in FIG. 2. At t=0, CO gas is introduced into the chamber and the CO sensor starts to respond. At $t=t_{thresh}$, the sensor response has reached the predetermined CO bump threshold, $R_{bump}$, and the gas monitor stops introducing test gas into the chamber.

In this case, the gas monitor is configured to continue to introduce gas into the chamber for a predetermined period of time or until the sensor has reached the bump threshold, $R_{bump}$.

If the sensor does not reach the bump threshold response in the predetermined period of time, the sensor is considered not to have met the requirements of the bump test. The gas monitor may be configured to provide an audio and/or visual indication that the gas monitor is no longer monitoring that gas.

In other embodiments, If the sensor does not reach the bump threshold response in the predetermined period of time, the gas monitor is configured to run a calibration test (see below) and then re-bump test the sensor. If the sensor does not reach the bump threshold response in the predetermined period of time after calibration, the sensor is considered not to have met the requirements of the bump test.

For a calibration, the gas monitor is configured to monitor the response of the corresponding gas sensor (e.g. the CO sensor when CO is introduced into the chamber). The calibration test curve 292 is shown in FIG. 2. In this case, the gas monitor is configured to determine the steady-state response of the sensor and then adjust the gas monitor accordingly.

In this case, the gas monitor is configured to continue to introduce test gas into the chamber for a predetermined period of time or until the sensor has reached a consistent response, $R_{cal}$. The response may be considered consistent if the response is not varying within a predetermined range (e.g. ±1%) over a predetermined period of time (e.g. 5 seconds).

The gas monitor is then configured to adjust itself based on the consistent response value, $R_{cal}$. For example, the gas monitor may be configured to scale the sensor response in detection mode based on the consistent response value to calculate the level of gas present. For example, if the calibration determines that the gas sensor was less responsive (and had a lower consistent response value, $R_{cal}$), a particular sensor response value in a detection mode could be associated with a higher level of gas to compensate for the decrease in sensitivity. Other sensors may comprise onboard electronics that provide a digital output. These sensors may be configured to calibrate the sensor's output when exposed to a known concentration of gas and placed in a calibration mode.

If the consistent response, $R_{cal}$, is below a predetermined threshold, the sensor is considered not to have met the requirements of the calibration. The gas monitor may be configured to provide an audio and/or visual indication that the gas monitor is no longer monitoring that gas.

The results of the tests are transmitted to a remote computer via transceiver 103.

Some embodiments may be configured to determine a measure of the inferred consistent response value, $R_{cal}$, based on the bump test curve. For example, a more rapid response (e.g. lower $T_{thresh}$) may be associated with a higher inferred consistent response value, $R_{cal,\ inf}$. In this way, if the inferred consistent response value, $R_{cal,\ inf}$ is sufficiently different from the last measured consistent response value, $R_{cal}$, the gas monitor may be configured to re-run a calibration test to re-measure the consistent response value, $R_{cal}$.

In some embodiments, the gas monitor may be configured to measure trends in bump test gas curves over time and determine when a calibration is due based on the determined trend. For example, a calibration may be scheduled based on the increase in $T_{thresh}$ over a series of bump tests. Because typically less gas is required for bump tests, predicting when calibration is needed from the bump tests may reduce the overall consumption of test gas. This may allow the gas monitor to remain in the field for longer.

In some embodiments, the gas monitor may be configured to measure trends in the bump test gas curves over time and determine when a sensor is nearing its end of life. In this way, for example, sensor replacement may be scheduled based on the increase in $T_{thresh}$ over a series of bump tests.

Other Options

In other embodiments, the transportable gas detector may comprise a camera to visually survey the environment. This may allow a remote user to assess the status of the gas detector without a site visit.

The transportable gas detector comprises a motion sensor. The transportable gas detector may be configured to send an alert to a remote computer in response to the detected motion meeting a predetermined criterion (e.g. corresponding to falling over). The alert may comprise location information. The transportable gas detector may have a transport mode which deactivates the motion sensor during transport. This may help reduce the number of unnecessary alerts being received at the remote computer. The transportable gas detector may be configured to send location information when the transport mode is turned off and the monitor is returned to normal operating mode.

The transportable gas detector may comprise a handle for lifting the gas detector. The handle may comprise a switch which is activated when the gas detector is lifted. The transportable gas detector may be configured to transmit location information to a remote computer when the handle and switch is released.

The gas detector comprises a wind sensor. The transportable gas detector may be configured to postpone switching to a test mode in response to the wind level exceeding a predetermined threshold. This may help reduce the instances where the wind is strong enough to blow the test gas out of the chamber, leading to an erroneous result that the gas sensor is no longer sensitive to the test gas. Other embodiments may be configured to include wind information with the test results. This may allow a user to decide remotely whether a particular test is reliable.

A gas detector may have one or more internal pumps and/or one or more solenoids to draw gas from different inlets. The gas detector may be designed to connect to a demand flow regulator connected to a cylinder. The cylinder would contain the appropriate bump test and/or calibration gas. The gas detector could be programed to initiate the bump test and switch to the appropriate gas inlet when a bump test or calibration is due.

Multiple inlets may be used in situations where the area monitor requires special gas (such as nitrogen) to zero the sensors before a particular calibration (such as a $CO_2$). In this situation a cylinder of zeroing gas and a cylinder of calibration gas would be connected to the area monitor. The area monitor would be programmed to automatically draw from the appropriate cylinder at the appropriate time.

The transportable gas detector may be configured to detect gases from a remote location by pumping gas from the remote location into the chamber via a gas line connected to an inlet.

In other embodiments, each sensor may be positioned within a separate chamber. This may help prevent test gas pumped to test one sensor from affecting the operation of another sensor (e.g. either during detection and/or testing of the other sensor). In this configuration, each gas may have a separate pump.

Although the present disclosure has been described and illustrated with respect to certain embodiments and uses thereof, it is not to be so limited since modifications and changes can be made therein which are within the full, intended scope of the disclosure as understood by those skilled in the art.

The invention claimed is:

1. A transportable gas detector unit comprising:
   a controller and a battery contained within the transportable gas detector unit;
   one or more source inlets for connection to one or more gas sources, said gas sources mounted on the transportable gas detector unit by mounting points on the transportable gas detector unit, the mounting points being configured to rigidly hold the gas sources in place when the transportable gas detector unit is moved;
   a chamber comprising a gas-permeable portion to allow gaseous communication with an outside environment and one or more source outlets configured to receive gas from the one or more source inlets;
   a gas sensor in communication with the controller and positioned within the chamber;
   a flow switch controlled by the controller, the flow switch configured to allow the received gas to be introduced directly into the chamber via the one or more source outlets; and
   a wireless transceiver configured to enable communication between the controller and a remote computer;
   wherein the transportable gas detector unit is configured to:
      in a detection mode, detect gases entering the chamber through the gas-permeable portion from the outside environment; and
      in a test mode, introduce gas via the one or more source outlets and test that the gas sensor is detecting the introduced gas; and
   wherein the transportable gas detector unit is moveable and includes a handle.

2. The transportable gas detector unit according to claim 1, wherein the transportable gas detector unit further comprises a pressure sensor configured to measure a gas pressure within the chamber when gas is being introduced into the chamber and to transmit an alert in response to the gas pressure exceeding a predetermined threshold.

3. The transportable gas detector unit according to claim 1, wherein the transportable gas detector unit is further configured to switch between the test mode and the detection mode in response to receiving a command remotely via the wireless transceiver.

4. The transportable gas detector unit according to claim 1, wherein the transportable gas detector unit is further configured to switch autonomously between the test mode and the detection mode.

5. The transportable gas detector unit according to claim 1, wherein the gas-permeable portion further comprises a mesh screen with mesh openings of less than 150 microns.

6. The transportable gas detector unit according to claim 1, wherein the handle has a handle switch which is activated when the transportable gas detector unit is lifted; and wherein the transportable gas detector unit is further configured to transmit location information to the remote computer in response to the handle being released.

7. The transportable gas detector unit according to claim 1, wherein the transportable gas detector unit is further configured to:
   perform a series of bump tests, each bump test comprising introducing a gas into the chamber and measuring a sensor response until a predetermined response threshold is reached;
   measure trends in the measured sensor response for each of the series of bump tests over time; and
   determine when a calibration is due based on the measured trends.

8. The transportable gas detector unit according to claim 1, wherein the transportable gas detector unit is further configured to:
- perform a series of bump tests, each bump test comprising introducing a gas into the chamber and measuring a sensor response until a predetermined response threshold is reached;
- measure trends in the measured sensor response for each of the series of bump tests over time; and
- determine when a sensor is nearing its end of life.

9. The transportable gas detector unit according to claim 1, wherein the transportable gas detector unit is further configured to:
- introduce a baseline gas into the chamber;
- measure a response of a sensor which is insensitive to the introduced baseline gas; and
- determine a baseline for said sensor based on the measured response to the introduced baseline gas.

10. The transportable gas detector unit according to claim 1, wherein the transportable gas detector unit further comprises a motion sensor.

11. The transportable gas detector unit according to claim 1, wherein the transportable gas detector unit further comprises a wind sensor.

12. The transportable gas detector unit according to claim 1, wherein the transportable gas detector unit further comprises a microphone.

13. The transportable gas detector unit according to claim 1, wherein the transportable gas detector unit further comprises a microphone and a speaker configured to sound an audio alarm when activated by the controller, the microphone being configured to detect whether the audio alarm is sounding when activated.

14. The transportable gas detector unit according to claim 1, wherein the transportable gas detector unit further comprises a pump configured to pump gases from one or more of the one or more source inlets into the chamber.

15. The transportable gas detector unit according to claim 1, wherein the transportable gas detector unit further comprises a renewable energy generator.

16. The transportable gas detector unit according to claim 1, wherein the transportable gas detector unit further comprises a plurality of gas sensors, each sensor being positioned within a separate chamber.

17. The transportable gas detector unit according to claim 1, wherein the transportable gas detector unit further comprises a plurality of gas sensors, each sensor being positioned within a common chamber.

* * * * *